United States Patent [19]

Young et al.

[11] Patent Number: 4,961,417

[45] Date of Patent: Oct. 9, 1990

[54] SURGICAL DRESSING

[75] Inventors: David E. Young, Watlington; Kenneth P. Davis, Hillington, both of England

[73] Assignee: Protectair Limited, Abingdon, England

[21] Appl. No.: 304,571

[22] Filed: Jan. 31, 1989

[30] Foreign Application Priority Data

Feb. 2, 1988 [GB] United Kingdom ............... 8802291

[51] Int. Cl.$^5$ ............................................. A61F 13/00
[52] U.S. Cl. .................................... 128/82; 604/175; 604/54
[58] Field of Search ............ 128/92 R, 92 Z, 92 Z X, 128/92 ZW, 92 ZY, 92 ZZ, 155, 157, 82; 604/93, 174, 175, 265; 606/54–59

[56] References Cited

U.S. PATENT DOCUMENTS

| 2,435,850 | 2/1948 | Siebrandt | 128/92 Z |
| 3,574,306 | 4/1971 | Alden | 604/162 |
| 3,877,424 | 4/1975 | Murray | 128/97 Z |
| 4,336,806 | 6/1982 | Eldridge, Jr. | 604/174 |
| 4,399,816 | 8/1983 | Spangler | 128/154 |
| 4,498,903 | 2/1985 | Mathew | 604/174 |
| 4,517,971 | 5/1985 | Sorbonne | 604/174 X |
| 4,583,976 | 4/1986 | Ferguson | 604/174 |
| 4,726,716 | 2/1988 | McQuire | 604/180 |

Primary Examiner—Mickey Yu
Assistant Examiner—Lynda M. Cofsky
Attorney, Agent, or Firm—Tilton, Fallon, Lungmus

[57] ABSTRACT

A surgical dressing adapted for fastening around orthopaedic fixator pins and similarly shaped surgical devices adjacent their sites of entry to and exit from the body, comprises a pad of resilient and absorbent material adapted to be folded around one or more fixator pins in apposition to the sites of entry and/or exit from the body; a friction member to be interposed between the pad and the fixator pins to inhibit movement of the pad along the fixator pins; and a clip adapted to be fastened around the fixator pins and at least a part of the resilient pad to clamp the pad in position around the pins.

5 Claims, 2 Drawing Sheets

SURGICAL DRESSING

This invention relates to surgical dressings for fastening around external fixator and traction pins and similarly shaped surgical devices at their sites of entry into the body, and which may be used to inhibit the entry of infection into the body at those sites.

In orthopaedic practice the use of metal pins is common. Such pins are used as components in external fixator systems for the management of fractures and leg lengthening procedures in children and also for applying traction. Pins are typically named for their inventors, such as Steinmann, Hoffman, Denham and Shantz.

In simple external fixators, one pin is driven through the soft tissue of the fractured limb into and through the bone above the fracture and out through the soft tissue on the other side and a second pin, parallel with the first, is driven through the soft tissue and bone below the fracture. Parts of both pins extend clear of each side of the limb, and serve for the attachment of tie bars having a series of holes. One tie bar fits over the exposed ends of both pins on one side of the limb, and another tie bar fits over the exposed ends of both pins on the other side of the limb. The tie bars are secured to the pins by screws in threaded holes which run into the holes carrying the pins.

More sophisticated external fixator systems have tie bars in two parts which slidably engage one another and can be locked into any position so that they may be used to distract or compress the fracture. Yet other systems employ multiple pins.

Traction pins are also driven right through a limb and the exposed ends are used as the drawbar in a traction set.

There is a clear need for a closed environment around the entry and exit wounds of external fixator and traction pins, since all pin wounds provide potential ingress for pathogens and infections at the points where the pins interface with skin are extremely common. The problem is often exacerbated when pins are loaded during traction. In these circumstances, skin proximal to the tractive force tends to be slightly compressed onto the pin whereas skin distal to the force tends to be either in light contact with the pin or to be held slightly away from it.

The pin path offers a potential path for virulent organisms, such as penicillinase producing staphylococci, to reach and attack bone. Osteomyelitis is notoriously difficult to eradicate even with modern specific antibiotics and any suitable new prophylactic measure, likely to reduce the occurrence, would be welcomed by orthopaedic surgeons and nurses.

The present inventors are aware of no device specifically developed for the purpose of treating the entry and exit wounds associated with orthopaedic external fixator pins. They are, however, aware that the current usual hospital practice is to carry out regular antiseptic toilet with sterile gauze swabs. These swabs are usually soaked at the point of use with cetrimide or some such similar compound. Topical antiseptics can be used but some can cause hypersensitivity; there are several compounds available to which the allergenic response is very low.

Although topical antibiotics can be used to treat local infections around pins, this is out of favour in hospitals because there is a risk of selecting resistant organisms. This makes more difficult the subsequent treatment of systemic infections due to these pathogens. In addition there is again the risk of causing hypersensitive skin reactions.

There are many vehicles employed both in hospital and community practice, for the topical administration of antiseptics and antibiotics including creams, ointments, sprays, aerosols and impregnated dressings of various types. There are also devices for the local treatment of wound infections including irrigation shields. The present invention is aimed mainly at preventing infection around orthopaedic pins but can be used with equal effect around the plastics drainage catheters used in general surgery.

The present inventors know of several devices, all having some characteristics in common and especially their circular plan form, which are designed for use around surgical wound drains. None of these is less than about 38 mm (1.5 inches) in diameter and this makes them unsuitable for many pin applications. This is because it is now common to use two pins within about 13 mm (0.5 inches) of one another on the same side of the fracture. An example of such a fixator is the EBI Orthofix R, made by Danielli Company in Milan, Italy.

One other factor that makes the round wound catheter support and dressing type of device unsuitable is the provision, in most cases, of an adhesive for application to the skin. In fractures where fixator pins are used, skin loss and other soft tissues lesions such as lacerations over the fracture site are extremely common and these will usually be a contraindication to the use of an adhesive.

The present invention seeks to provide a wound treatment device specifically structured for use at the entry and exit wounds of single and multiple fixator pins used in orthopaedic practice.

According to the invention, there is provided a surgical dressing adapted for fastening around orthopaedic fixator pins and similarly shaped surgical devices adjacent their sites of entry to and exit from the body, the dressing comprising a pad of a resilient and absorbent material adapted to be folded around one or more fixator pins in apposition to the sites of entry to and/or exit from the body;

friction means to be interposed between the pad and the fixator pins to inhibit movement of the pad along the fixator pins; and a clip adapted to be fastened around the fixator pins and at least a part of the resilient pad to clamp the pad in position around the pins.

In accordance with a first embodiment of the invention, the dressing for use at the entry and exit wounds of metal orthopaedic pins comprises a pad of soft open cell polyurethane foam, skinned on one side, substantially rectangular in shape and with a deep but narrow relieved zone formed centrally along one long edge. A series of holes is formed in the pad a small distance in from the same long edge.

A strip of plastics film having a latex coating on one side and an adhesive coating on the other is secured to the unskinned face of the dressing pad. The plastics strip has a series of identically sized and spaced holes along its length and is adhered to the pad so that the holes in the pad and the strip are in registry.

A multiple clip for use with this pad is of plastics material and is conveniently formed by injection moulding. It is in the form of a narrow strip with a central folding or hinging zone which effectively divides the clip into two functional areas. One functional area has a series of protrusions on its inner surface which function as latches, and the other functional area has a corresponding series of holes which function as rim catches. Again, the latches and catches will be identically sized and spaced along the length of the clip so as to be able to register with the holes in the pad and the strip. The clip is conveniently assembled to the foam pad and the plastics strip by rivetting.

The dressing is applied by folding the assembled components around one or more orthopaedic pins close to their entry or exit wounds. The lower edge of the foam pad is pressed gently against the skin and the multiple clip is then closed. As a result, the latex coating of the film strip is pressed against the pins, presenting a non-slip surface, thus preventing the dressing from riding up the pins.

In accordance with a second preferred embodiment, the dressing comprises a pad of soft open cell polyurethane foam, skinned on one side and of rectangular shape but without the relieved zone or series of holes described above. As with the embodiment described above, however, the foam pad carries adhered to its unskinned surface along its edge which after application of the dressing, will be remote from the entry or exit wounds, a strip of plastics film presenting a latex surface.

In this preferred embodiment, the clip comprises a generally rectangular substantially rigid injection moulded plastics member which is longer but narrower than the foam pad and provided at its ends with suitable latching means and intermediate its length with a hinge mechanism. The latching means is suitably of relatively straightforward construction, for example a simple snap fastening, since it is required to withstand only a relatively small opening force and relatively few openings and closings before the whole device is discarded. Similarly, the hinge mechanism is suitably provided merely by reducing the thickness and, if necessary, the width of the plastics member in the hinging zone, again since the hinge will be required to withstand relatively few openings and closings of the clip.

The pad may, if desired, be secured to the clip by means of one or more plastics rivets which may be formed integrally with the clip, or by means of an adhesive. In this case, the dressing is applied by folding the assembled components about the hinge formed in the clip, around one or more orthopaedic pins close to their entry or exit wounds. The lower edge of the foam pad is pressed gently against the skin and the clip is then closed by latching together the free ends of the clip.

The second embodiment described above has the advantage that fastening and unfastening of the dressing involves only a single latching or unlatching operation which in turn involves less risk of the fixator pins being knocked or otherwise disturbed and causing physical damage or discomfort to the patient. Also, the dressing according to the second embodiment can be made in a variety of lengths to suit the requirements of any particular number and spacing of fixator pins; in contrast, the dressing of the first embodiment may not always be suitable if the spacing of the latches is such as to interfere with the fixator pins.

The foam pad can be impregnated with an antiseptic of known low allergenicity such as providone, pyrollidone, iodine or chlorhexidine acetate in an aqueous base. It is important to note that, if this is done, the amount of antiseptic should be moderate in comparison with the total absorbent load which the pad can carry. This ensures that the pad will still be able to take up an appreciable quantity of exudate from the entry or exit wounds.

The assembled dressing will generally be presented in a sterile package from which it can be readily removed immediately before its application.

The present invention will now be described in greater detail by way of example only with reference to the accompanying drawings in which.

Figure 1:
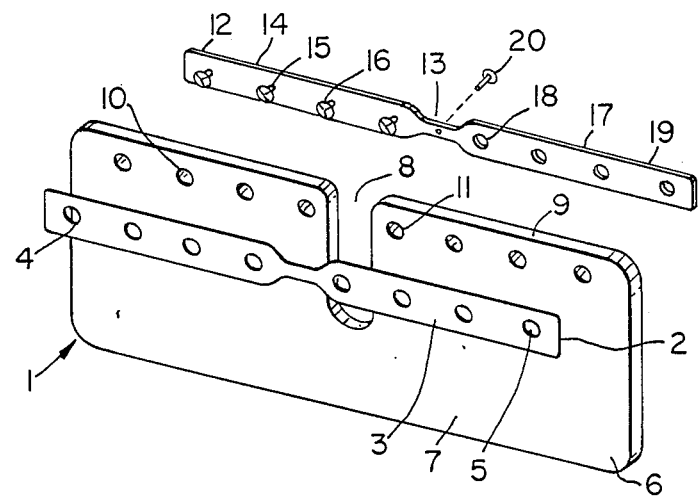
FIG. 1 is an exploded view of a first dressing according to the invention.

Referring first to FIG. 1 of the drawings, a dressing 1 for metal orthopaedic pins includes a plastics strip 2 with an inner latex lining 3 (indicated by cross hatching) and an outer coating of adhesive (not visible). A series of holes indicated at 4 and 5 is spaced evenly along the plastics strip 2.

The dressing includes also a pad 6 of soft medical grade open cell polyurethane which is unskinned on its inner surface 7 and skinned on its outer surface (not visible). Foam pad 6 is generally rectangular in shape with rounded corners and has a deep narrow cutaway 8 in its upper long edge 9. It is produced by die-cutting on a clicking press from a sheet of single skinned foam.

A series of holes indicated at 10 and 11 is spaced evenly along foam pad 6, adjacent its upper long edge 9, having the same centres as and corresponding with the series of holes indicated at 4 and 5 in the plastics strip.

A multiple clip 12, made of plastics by injection moulding, is generally of narrow rectangular shape with rounded corners. A waisted section 13 acts as a flexible hinge. One end 14 of the multiple clip 12 carries a series of projections indicated at 15 and 16, which function as latches and the other end 17 of the multiple clip 12 has a series of holes indicated at 18 and 19, which function as rim catches.

The projections 15 and 16 and the holes 18 and 19 have the same centres as the holes 10 and 11 in foam pad 6 and the holes 4 and 5 in plastics strip 2.

The dressing is assembled by attaching the strip 2 by means of the adhesive coating on its outer surface to the inner unskinned surface 7 of the foam pad 6 adjacent its upper long edge 9 so that the holes 4 and 5 of the strip 2 and the holes 10 and 11 in the foam pad 6 are in registry. The multiple clip 12 is then attached to the outer skinned surface of the foam pad 6 adjacent to its upper long edge 9 by passing the projections 15 and 16 through the holes 10 and 4 in the foam pad 6 and the strip 2, respectively, so that the holes 18 and 19 align with the holes 11 and 5 in the foam pad 6 and strip 2, respectively. The multiple clip 12 is then secured in place by passing a small plastics rivet 20 through small aligned holes in the waisted section 13 of the clip 12 and in the central region of the strip 2 which overlies the cutaway 8 in the foam pad 6.

In use, the assembled dressing 1 is folded around the pin or pins, gently pressed down onto the patients skin and clipped into place by squeezing together end 14 and end 17 of multiple clip 12. Latex coating 3 provides a non-slip surface and prevents the dressing device 1 from riding up the pins.

Figure 2:
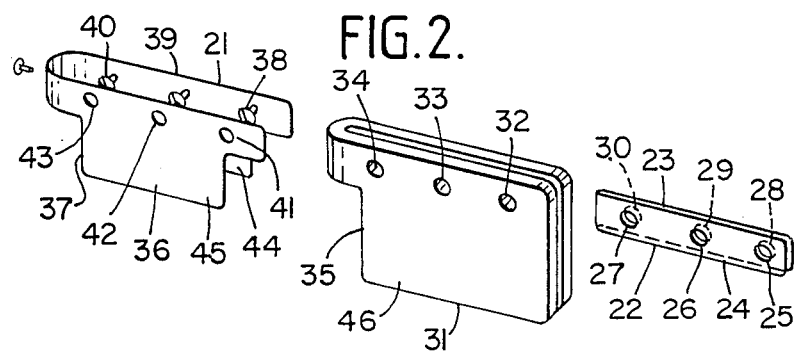
FIG. 2 is an exploded view of a second dressing according to the invention.

Turning now to FIG. 2, there is shown an exploded view of an alternative dressing 21 in the folded condition. Dressing 21 includes a plastics strip 22 with a latex coating 23 (shown by cross hatching) on its inner surface and adhesive coating 24 on its outer surface. Plastics strip 22 also has spaced holes 25, 26, 27, 28, 29 and 30.

Foam pad 31 has a corresponding series of holes of which three are visible at 32, 33 and 34, and a cutaway at 35.

Clip 36 has a waisted section at 37 which acts as a hinge. Projections 38, 39 and 40 function as latches and engage holes 41, 42 and 43 when the dressing 21 is clipped into place over metal orthopaedic pins. Skirts 44 and 45 on clip 36 are downward extensions which end short of the lower margin 46 of the foam pad 31.

The function of the two embodiments is identical and the principles are the same. However, skirts 44 and 45 confer increased rigidity and slightly easier handling at the expense of slight loss of conformability, especially over acutely curved areas of the patient's body.

Figure 3:
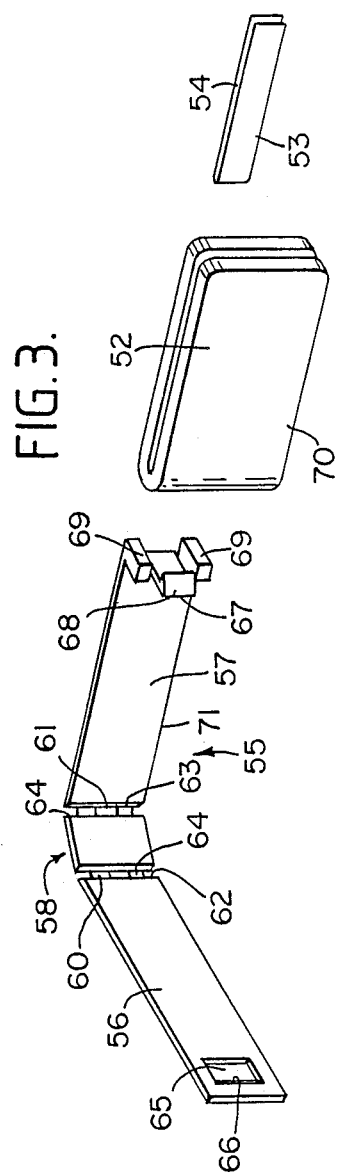
FIG. 3 is an exploded view of a third, preferred, dressing according to the invention.

In the dressing 51 shown in FIG. 3, a foam pad 52 of generally rectangular shape and an adhesive strip 53 carrying a latex coating 54 on its inner surface, are similar to the pads 6 and 31 and strips 2 and 22 of the dressings shown in FIGS. 1 and 2, respectively, except that they have no holes in them. In this instance, the clip for fastening the dressing passes completely around the pad.

Figure 4:
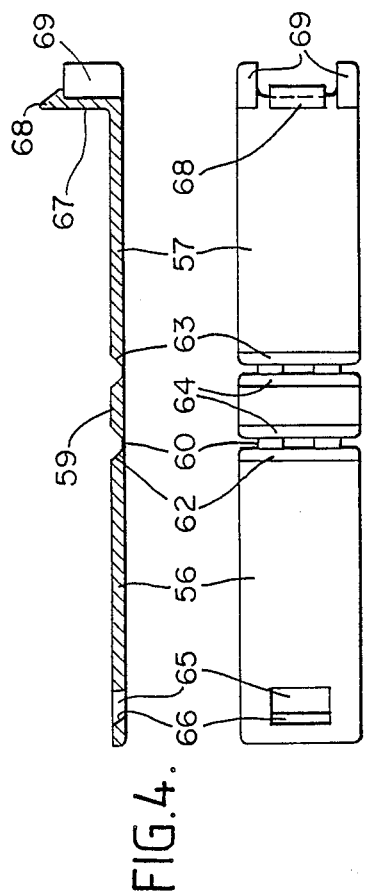
FIG. 4 is a side sectional view and a plan view of the clip used in the dressing of FIG. 3.

The clip 55 is shown in FIG. 3 in a partially opened position and is shown also in plan and side sectional elevations in FIG. 4. It consists of an injection moulded plastics material, for example polypropylene, in the form of an elongate strip having a central hinge mechanism 58 and latching elements including a latch tongue 67 and a latch slot 65 adjacent its ends.

More particularly, the clip 55 consists of clip arms 56 and 57 connected together by a hinge mechanism 58 which includes a body element 59 and two pairs 60 and 61 of flexible webs about which the clip can be folded around the foam pad 52. The ends 62, 63 and 64 of the arms 56 and 57 and of the hinge body 59 are angled so as not to hinder or obstruct the folding of the clip. The left hand arm 56 of the clip (from the view point of FIG. 4) contains adjacent its free end, a rectangular slot 65 with an inclined wall 66. The right hand arm 57 of the clip has an upstanding tongue 67 with a bevelled and overhanging upper edge 68 and a width corresponding to the width of the slot 65. On each side of the tongue 67 there is an upstanding shoulder 69.

The pad 52 with its adhered strip 53 is preferably attached to the clip 55, for example adhesively and the whole is preferably presented within a sterile package.

The length of the arms 56 and 57 is slightly greater than that of the folded pad 52 to enable the pad 52 to be accommodated within the fastened clip. Also, the width of the clip 55 is less than that of the pad 52 to enable the lower margin 70 of the pad to extend freely below the lower edge 71 of the clip.

To fasten the dressing around the pin or pins, the clip and pad are folded about the hinge of the clip around the pins and the slot 65 is passed over the tongue 67 and pushed against the shoulder 69 so that the overhanging upper edge 68 of the tongue 67 is engaged by the slot 65. The natural resilience of the pad 52 will then bias apart the arms 56 and 57 to secure the clip in its fastened state.

Alternative embodiments of the dressing according to the invention can easily be contemplated, for example including separate pads each with their own adhering strips and separate but cooperating parts of a clip by means of which the two pads can be fastened securely around the pin or pins.

We claim:

1. A surgical dressing adapted for fastening around orthopaedic fixator pins adjacent their sites of entry to and exit from the body, the dressing comprising
   a pad of resilient and absorbent material adapted to be folded around one or more fixator pins in apposition to the sites of entry to and/or exit from the body and having a lower margin for body contact at such sites when said pad is so folded;
   friction means along a surface of said pad for frictional engagement with one or more; fixator pins when said pad is folded round such pins; and
   a clip adapted to be fastened around said resilient pad to clamp the pad in folded position around one or more fixator pins; said clip having a width less than that of said pad and being fastened around said pad when the same is folded with said lower margin of said pad being extended below said clip and exposed for body contact.

2. A surgical dressing according to claim 1, wherein the resilient pad is of open cell plastics foam.

3. A surgical dressing according to claim 1 wherein the friction means is a latex strip adhered to said one surface of said resilient pad.

4. A surgical dressing according to any one of claims 1 to 3, wherein said clip is in the form of a flexible strip with spaced holes constituting catches along one half of its length and identically spaced projections constituting latches along the other half of its length, and wherein said resilient pad includes identically spaced holes through which the latches of the clip can be passed to engage with the catches and clamp the pad in position.

5. A surgical dressing according to any one of claims 1 to 3, wherein the clip is in the form of a strip with a catch aperture adjacent its one end and a latch projection adjacent its other end and a hinge intermediate its two ends, the strip being foldable about said hinge to extend completely around the pad when the same is folded to enable the latch to be engaged by the catch and clamp the pad in position.

* * * * *